United States Patent [19]

Shimura et al.

[11] Patent Number: 5,105,816
[45] Date of Patent: Apr. 21, 1992

[54] METHOD AND SYSTEM FOR MAKING BLOOD FLOW VISIBLE

[75] Inventors: Takaki Shimura, Machida; Keiichi Murakami, Kawasaki; Shinichi Amemiya, Yokohama, all of Japan

[73] Assignee: Fujitsu Limited, Kawasaki, Japan

[21] Appl. No.: 525,054

[22] Filed: May 18, 1990

[30] Foreign Application Priority Data

May 20, 1989 [JP] Japan ................................. 1-127586

[51] Int. Cl.⁵ .............................................. A61B 8/06
[52] U.S. Cl. ............................. 128/661.08; 73/861.25
[58] Field of Search .................... 128/660.01, 660.05, 128/660.07, 661.04, 661.07–661.10, 662.01–662.02; 73/861.25

[56] References Cited

U.S. PATENT DOCUMENTS 4,790,321 12/1988 Miwa et al. ................. 73/861.25 X
5,010,528 4/1991 Ohtsuki et al. ............. 128/661.09 X

FOREIGN PATENT DOCUMENTS 62-224334 10/1987 Japan .

OTHER PUBLICATIONS

Ganong, W. F. "Review of Medical Physiology", Long Medical Publications, Los Altos Col. 94022 © 1983 p. 453.
Duran, C. et al. "Recent Progress in Mitral Valve Disease", Butterworths, London, England © 1984, pp. 13–59.
Japanese Ultrasonic Medical Society papers 48-C-20, 48-C-21, 51-PB-35 and 49-B-94, and English Abstracts.
Shigeo Ohtsuki et al., Automedica pp. 41–52.

Primary Examiner—Francis Jaworski
Attorney, Agent, or Firm—Staas & Halsey

[57] ABSTRACT

A method and system for making visible a flow of blood in a living body. The method comprises the steps of obtaining blood flow vector distribution maps by a recpetion of waves reflected from a living body to which ultrasonic pulses are radiated, and by a Doppler analysis of the reflected waves, arranging dummy blood corpuscle in domains in which the blood flow vector distribution maps are expressed, calculating flow velocity vector of the dummy blood corpuscle for each dummy blood corpuscle from the blood flow vector distribution maps, forming a plurality of images in which the dummy blood corpuscles are sequentially moved in response to the flow velocity vectors, and sequentially displaying the plurality of images on a display. Also, the density of the arrangement of the dummy blood corpuscles, for example, corresponds to the blood pressure.

13 Claims, 7 Drawing Sheets

METHOD AND SYSTEM FOR MAKING BLOOD FLOW VISIBLE

BACKGROUND OF THE INVENTION

1. Field of the Invention

The present invention relates to a method and system for making the flow of blood visible, whereby the flow of blood in a living body can be clearly seen.

2. Description of the Related Art

Ultrasonic diagnostic apparatuses are increasingly and widely used in the clinical field, not only for a tomogram (B mode image), but also for a Doppler analysis when for measuring a flow of blood in a heart lumen or a blood vessel. Particularly, recently the use of a color display of a real time blood flow velocity distribution, called color flow mapping, is rapidly spreading, since the display displays a flow of blood in a heart lumen as a color display, and thus a detection of a ventricular septal defect or valve failure can be made at a glance.

The real time image in this color flow mapping, however, displays only the following aspects. Namely, the blood flow at each position is displayed as a color code in response to the flow toward or flow away from an ultrasonic probe, or an amount of the component of the flow direction, for example, toward a direction corresponding to red (R), in an away direction corresponding to blue (B), and this amount corresponds to a brightness. Accordingly, a problem arises in that, when the real time images are continuously displayed, an image of the flow of blood is not obtained.

Recently, Motoyoshi Okujima, Shigeo Ohtsuki (Tokyo Institute of Technology), and Motonao Tanaka et. al. (Tohoku University) disclosed a blood flow vector generation process by which a vector distribution map is obtained in the real time flow from information on only a flow amount toward or a flow amount away from an ultrasonic probe (see Japan Ultrasonic Medical Society paper, May, 1986, 48-C-20, 48-C-21; November, 1987, 51-PB-35). As shown in this paper, each group obtains vector distribution maps at a plurality of phases. Nevertheless, when the maps are continuously displayed, the image of the real time blood flow cannot be seen.

Accordingly, a display of the flow of blood expressed by animated pictures is desired, as since the flow of blood relates to a blood pressure, at each position, and since the blood flow and the blood pressure are necessary for an analysis of the movement of a heart muscle or blood vessel, both the blood flow and the blood pressure distribution must be made visible.

SUMMARY OF THE INVENTION

An object of this invention is to understandably display a behavior of a blood flow and a blood pressure using an animation method, by an introduction of dummy blood corpuscles, a sequential movement of the dummy blood corpuscles in response to the blood flow, and further, the location of the dummy blood corpuscles, the density of which corresponds to the blood pressure.

In an aspect of this invention, there is provided a method for making visible a flow of blood in a living body, comprising the steps of obtaining blood flow vector distribution maps by a reception of reflecting waves from a living body to which ultrasonic pulses are radiated, and by a Doppler analysis of the reflecting waves; arranging dummy blood corpuscles in domains in which the blood flow vector distribution maps are expressed; calculating flow velocity vectors of the dummy blood corpuscle for each dummy blood corpuscle from the blood flow vector distribution maps; forming a plurality of images in which the dummy blood corpuscles are sequentially moved in response to the flow velocity vectors; and sequentially displaying the plurality of images on a display.

In another aspect of the invention, there is provided a system for making visible a flow of blood in a living body, comprising an ultrasonic transmission/reception means for radiating ultrasonic pulses to a living body, receiving reflecting waves from the living body, Doppler analyzing the reflecting waves, and carrying out processes to form vectors to thereby obtain blood flow vector distribution maps; a two-dimensional vector memory means for storing the blood flow vector distribution maps from the ultrasonic transmission/reception means; a calculation means for calculating data from the two-dimensional vector memory means and forming a two-dimensional dynamic pressure distribution map; a two-dimensional pressure distribution memory means for storing an output of the calculation means; a dummy blood corpuscle generation means for receiving an output of the two-dimensional pressure distribution memory means and forming dummy blood corpuscles in response to the output of the two-dimensional pressure distribution memory means; a two-dimensional dummy blood corpuscle distribution memory means for storing a two-dimensional distribution of an output of the dummy blood corpuscle generation means; a dummy blood corpuscles moving processor for receiving data from the two-dimensional dummy blood corpuscle distribution memory means and an output from the two-dimensional vector memory means, and for forming flow velocity vectors of the dummy blood corpuscle for each dummy blood corpuscle from the blood flow vectors of the blood flow vector distribution map; and a moving dummy blood corpuscle memory means for storing the respective images obtained by sequentially moving the dummy blood corpuscles by an amount in response to the flow velocity vector; whereby outputs of the moving dummy blood corpuscle memory means are sequentially read and a movement of the blood flow is detected.

DESCRIPTION OF THE PREFERRED EMBODIMENTS

A constitution and an operation of an embodiment according to this invention are explained in detail with reference to drawings.

Figure 1:
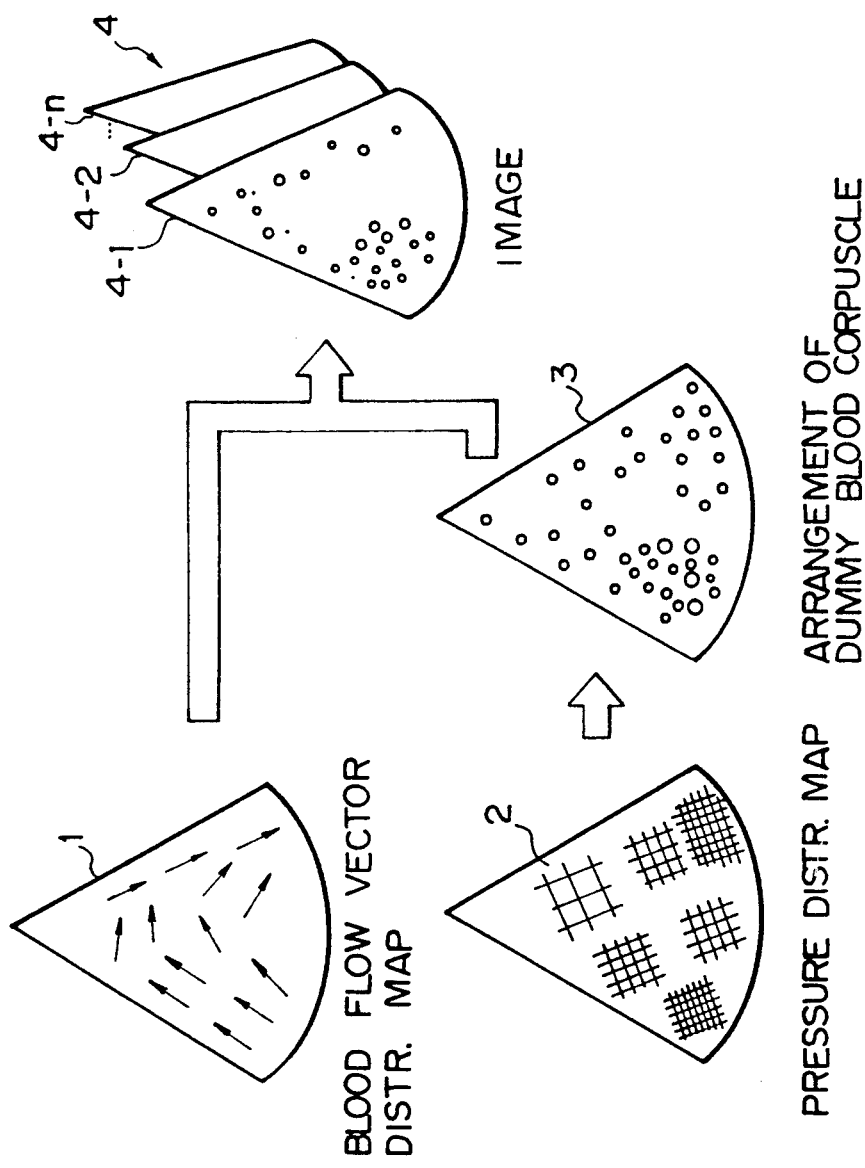
FIG. 1 is an explanatory diagram showing an embodiment according to this invention.

In FIG. 1, reference numeral 1 shows a blood flow vector distribution map. In this map, a magnitude and a direction of a blood flow velocity vector are expressed by using arrow marks as a blood flow vector distribution map obtained by receiving waves reflected from a living body radiated with an ultrasonic pulse, by Doppler analyzing the reflected wave, and by processing the forming of a vector.

In FIG. 1, reference numeral 2 shows a pressure distribution map. In the map, a distribution of a blood pressure in the living body is expressed. The distribution map is obtained, for example, by receiving waves reflected from the living body radiated with an ultrasonic pulse, by Doppler analyzing the reflected wave, by processing the analyzed data to obtain a two-dimensional Doppler velocity distribution, and further, using a method disclosed by Okujima, Ohtsuki, Tanaka, et. al (see Japan Ultrasonic Medical Society paper, October, 1986, 49-B-94). The obtained distribution map is a two-dimensional dynamic pressure distribution map. In FIG. 1, the high pressure is expressed by the high density of lines and the low pressure is expressed by the low density of lines.

In FIG. 1, reference numeral 3 is a map showing an arrangement of dummy blood corpuscles. In the map, a density (number per unit area) of the dummy blood corpuscles corresponds to a pressure value of the blood pressure distribution map 2.

In FIG. 1, reference numeral 4 shows an image 4 wherein the dummy blood corpuscles move in correspondence to the flow of blood. In this map, flow velocity vectors of the dummy blood corpuscles arranged as shown in the map 3 are obtained from the blood flow vector data in the blood flow vector distribution map 1 in FIG. 1 or from interpolated data of the above data, and then a plurality of pictures 4-1 to 4-n are formed by moving the dummy blood corpuscles in correspondence to the above obtained flow velocity vectors.

Next, the processes shown in FIG. 1 are explained with reference to FIG. 2.

Figure 2:
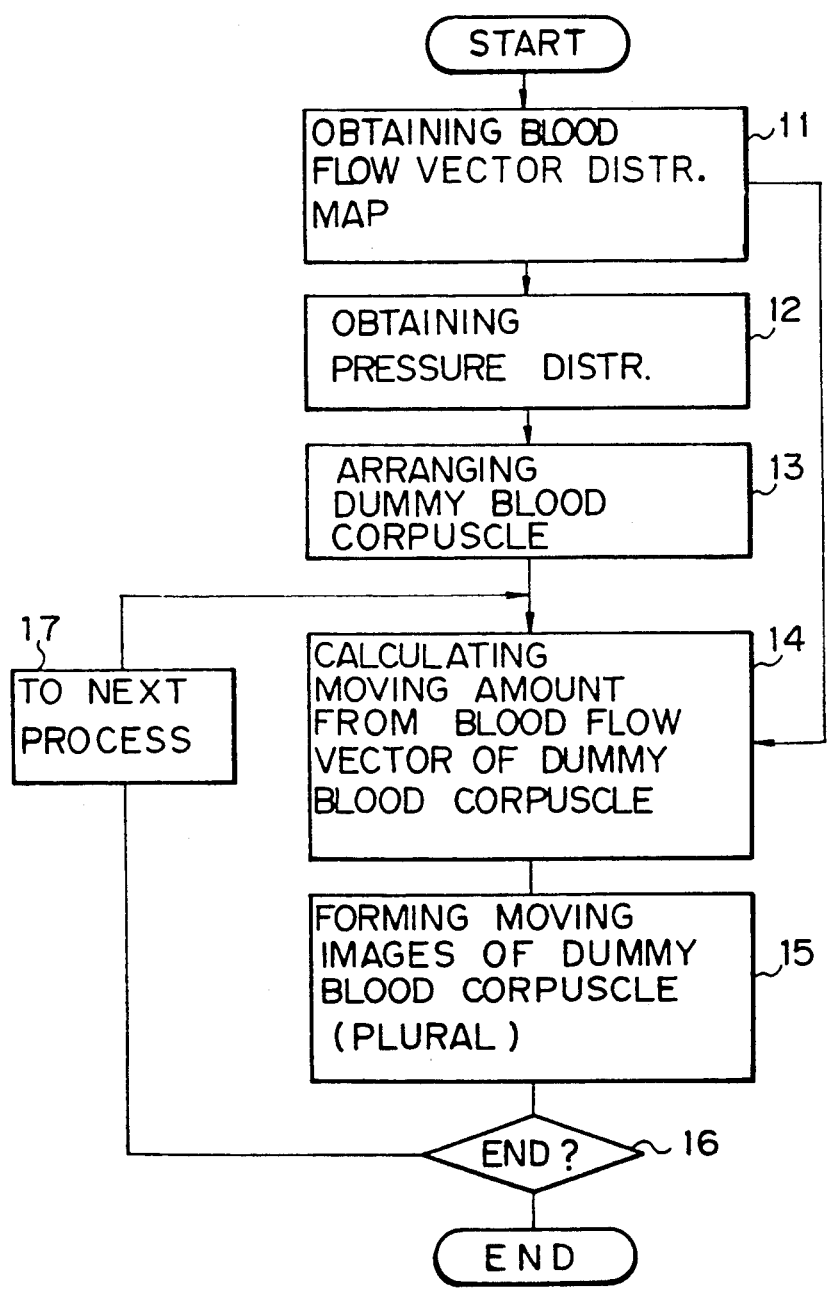
FIG. 2 is a flowchart showing processing steps in the embodiment of FIG. 1.

In FIG. 2, the blood flow vector distribution map in the living body is obtained in step 11. This map is the blood flow vector distribution map 1 in FIG. 1. In more detail, the ultrasonic pulse is radiated to the blood flowing in the living body, the reflected ultrasonic wave is received and Doppler analyzed, and the two-dimensional Doppler velocity distribution is obtained by calculating a flow velocity component toward or away from the probe for the blood by many points. From the above distribution, the blood flow vector distribution map 1 is obtained by the process of forming the blood flow vector disclosed by Ohtsuki et al.

In step 12, the pressure distribution is obtained. Namely, the two-dimensional dynamic pressure distribution map is formed from the above two-dimensional Doppler velocity distribution by the Ohtsuki et al. method.

In step 13, the dummy blood corpuscles are arranged. Namely, the number of dummy blood corpuscles corresponding to the pressure magnitude in the pressure distribution map 2 in FIG. 1 is located as shown in FIG. 1.

In step 14, the amount of movement of the dummy blood corpuscle is calculated from the blood flow vector data corresponding to the dummy blood corpuscle.

In step 15, the moving image of the dummy blood corpuscle is formed. Namely, as shown in the arrangement of the dummy blood corpuscle in FIG. 1, the moving image 4 moved by the amount of movement of the respective dummy blood corpuscles, which is calculated at step 14, are sequentially formed in correspondence to the arranged dummy corpuscles. By a sequential display of the plurality of images 4-1 to 4-n, the dummy blood corpuscles can be moved in proportion to the magnitude of the blood flow vector, and a behavior of the blood flow vector can be displayed as animated pictures.

Figure 7:
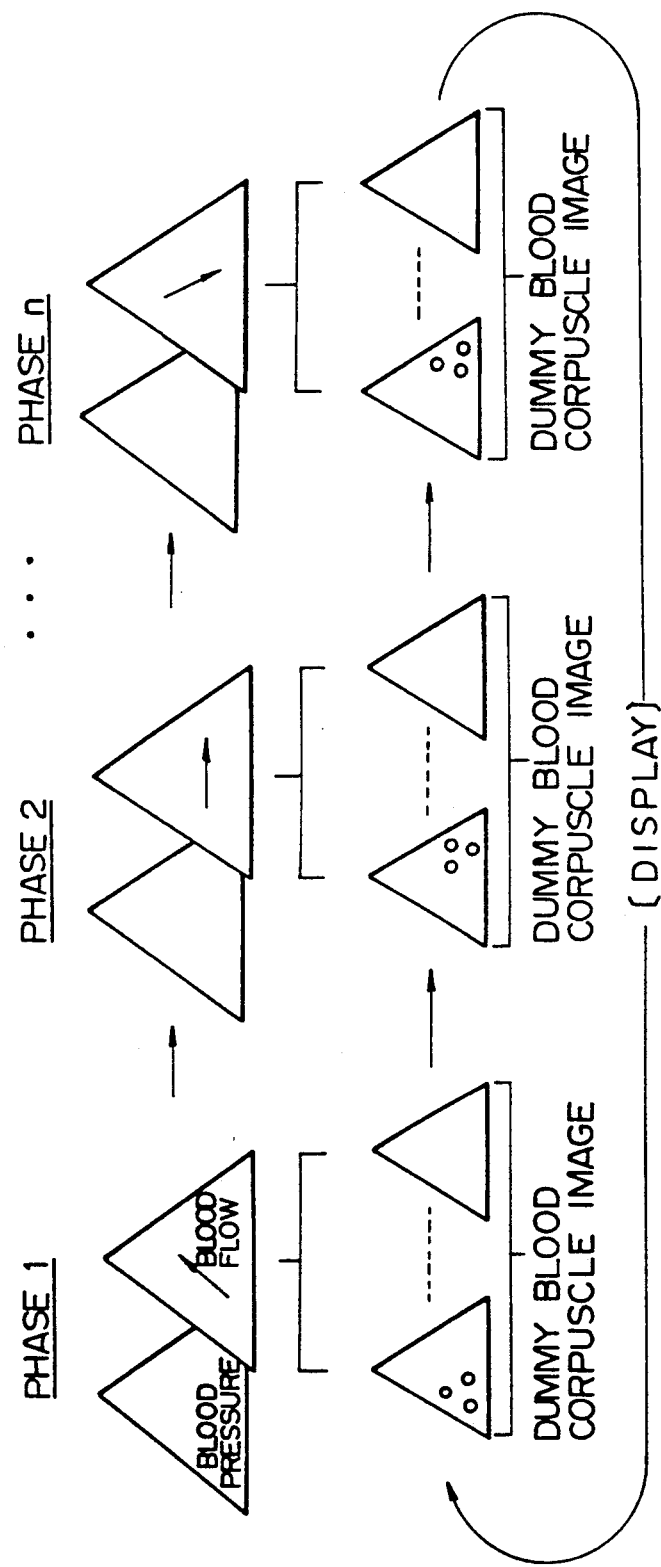
FIG. 7 is an explanatory diagram displaying a plurality of images according to the embodiment.

In step 16, the end is determined, and if the result is YES, the process is ended. If the results is NO, the process proceeds to step 17 and the steps 14 and 15 are repeated for the next process (e.g., next phase). The respective images 4 are formed sequentially at phase 1, phase 2, ... , phase n, as shown in FIG. 7.

Figure 3:
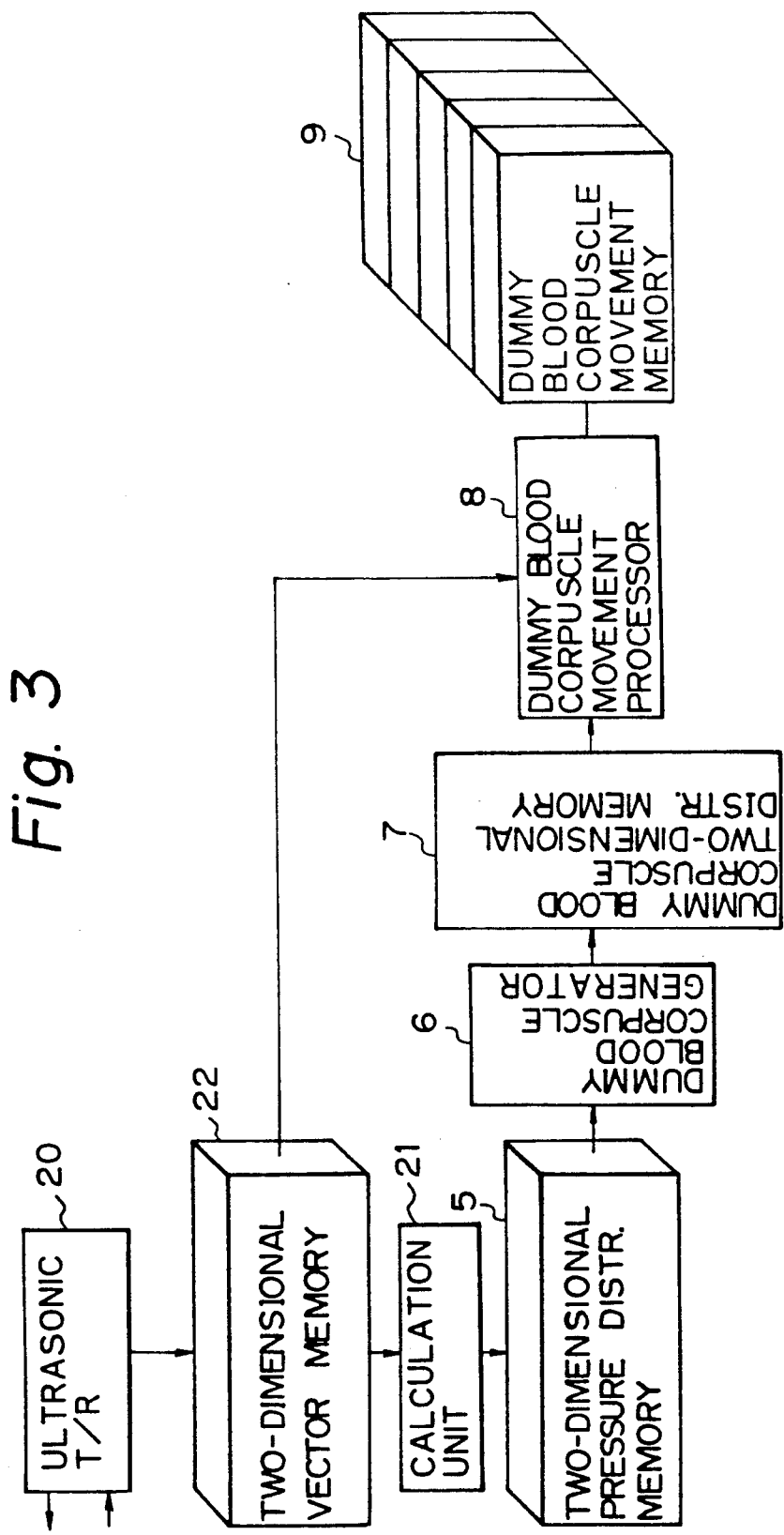
FIG. 3 is a block diagram showing a system of the embodiment of FIG. 1.

In FIG. 3, a constitution of a system according to this invention is shown.

This system comprises an ultrasonic transmitter/receiver 20, a two-dimensional vector memory 22, a two-dimensional pressure distribution memory 5, a calculation unit 21 between the memories 22 and 5, a dummy blood corpuscle generator 6, a dummy blood corpuscle two-dimensional distribution memory 7, a dummy blood corpuscle movement processor 8, and a dummy blood corpuscle movement memory 9.

The two-dimensional vector memory 22 is identical to the memory for storing the blood flow vector distribution map 1 in FIG. 1, and the two-dimensional pressure distribution memory 5 is the same as the memory for storing the pressure distribution map 2 in FIG. 1. The dummy blood corpuscle generator 6 generates the dummy blood corpuscles.

The dummy blood corpuscle two-dimensional distribution memory 7 is used for storing the dummy blood corpuscles in the arrangement of the dummy blood corpuscles shown in FIG. 1, and the memory 7 stores the dummy blood corpuscles generated by the dummy blood corpuscle generator 6.

The dummy blood corpuscle movement processor 8 obtains a flow velocity vector of the corresponding dummy blood corpuscles stored in the two-dimensional vector distribution memory 7 from the blood flow vector of the blood flow vector distribution map 1 stored in the two-dimensional vector memory 22, and forms images 4-1 to 4-n wherein the dummy blood corpuscles are sequentially moved by the above-obtained flow velocity vector magnitude.

The dummy blood corpuscle movement memory 9 is used for storing the images 4-1 to 4-n in FIG. 1, which are formed by the dummy blood corpuscle movement processor 8.

As mentioned above, by sequentially picking up and displaying the images 4-1 to 4-n stored in the dummy blood corpuscle movement memory 9, the dummy blood corpuscle can be moved sequentially as animated pictures in accordance with the flow velocity corresponding to the magnitude and direction of the blood flow vector, and further, the dummy blood corpuscle, the number of which corresponds to the blood pressure, can be sequentially moved as animated pictures, and thus the blood flow and the blood pressure can be understandably displayed.

An example of the generation of the dummy blood corpuscle is explained below. The dummy blood corpuscle is introduced for the convenience of the display and does not actually exist. First, the dummy blood corpuscles are arranged at each point of coordinates, one by one. Each dummy blood corpuscle is allotted one of the uniform random numbers, and then the number corresponding to the blood pressure value in the point of the coordinates is determined. The allotted uniform random numbers are selected by the threshold value, which is the above determined number corresponding to the blood pressure value. The dummy blood corpuscles of the coordinates having uniform random numbers less than the threshold value are remaindered and the others are eliminated. Then, as mentioned above, the dummy blood corpuscle is introduced.

The coordinates may be fixed to the display pixel, but a recognition of blood movement is obtained if the pitches of the coordinates are made larger than those of the display pixel. Further, the size of the dummy blood corpuscle is preferably larger than that of the pixel. Namely, the corpuscle is formed by a circle, triangle or colored circle made by several pixels, for example.

The amount of data of the blood flow vector is not sufficient, the following necessary processing is carried out. At this time, the flow velocity vector of the dummy blood corpuscle is obtained by interpolation from four adjacent blood flow vectors.

Figure 4A:
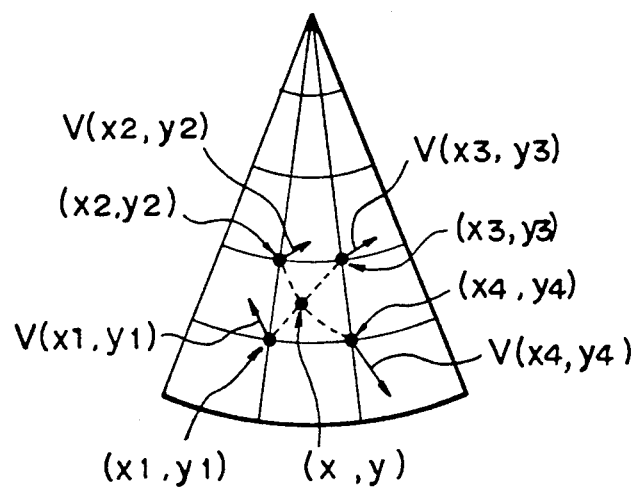
FIGS. 4A and 4B are explanatory diagrams showing an example of a calculation used to obtain a flow velocity vector of dummy blood corpuscles by interpolation.
Figure 4B:
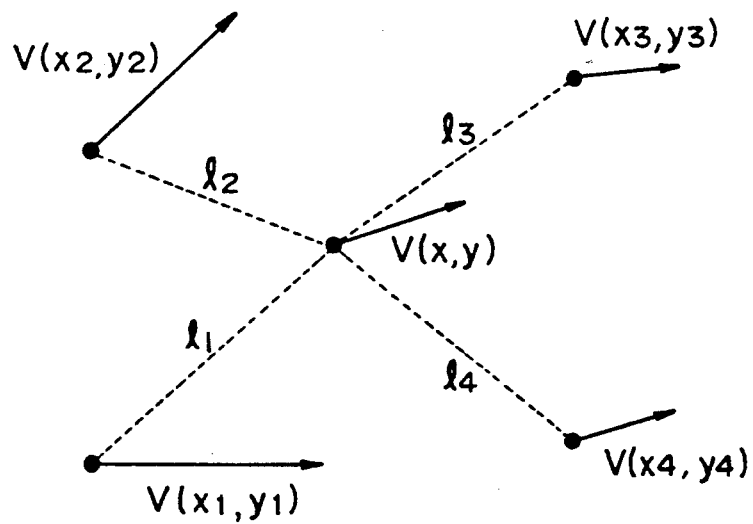

In FIG. 4A, it is assumed that the coordinates of the dummy blood corpuscle are (X, Y) and the blood flow vectors are $V_{(X1, Y1)}$, $V_{(X2, Y2)}$, $V_{(X3, Y3)}$, and $V_{(X4, Y4)}$.

The blood flow vectors $V_{(X1, Y1)}$ and $V_{(X3, Y3)}$ located diagonally opposite to each other are picked up. At this point, the distances between the positions (coordinates (X, Y)) are assumed to be $l_1$ and $l_3$, respectively. Then, as shown in equations (1) and (2), the blood flow vectors $V_{(X1, Y1)}$ $V_{(X3, Y3)}$ are analyzed to components X and Y, respectively.

$$V_{(X1, Y1)} = V_{X(X1, Y1)} + V_{Y(X1, Y1)} \quad (1)$$

$$V_{(X3, Y3)} = V_{X(X3, Y3)} + V_{Y(X3, Y3)} \quad (2)$$

The same operations are applied to the vectors $V_{(X2, Y2)}$ and $V_{(X4, Y4)}$, and thus the interpolation value as shown the following equation (3) is $$V_{(X,Y)} = \left( \frac{1}{1/l_1 + 1/l_2 + 1/l_3 + 1/l_4} \right) \times (1/l_1 \times V_{(X1,Y1)} + 1/l_2 \times V_{(X2,Y2)} + 1/l_3 \times V_{(X3,Y3)} + 1/l_4 \times V_{(X4,Y4)}) =$$

$$\left( \frac{1}{l_2 \times l_3 \times l_4 + l_1 \times l_3 \times l_4 + l_1 \times l_2 \times l_4 + l_1 \times l_2 \times l_3} \times (l_2 \times l_3 \times l_4 \times V_{(X1,Y1)} + l_1 \times l_3 \times l_4 \times V_{(X2,Y2)} + l_1 \times l_2 \times l_4 \times V_{(X3,Y3)} + l_1 \times l_2 \times l_3 \times V_{(X4,Y4)}) \right) \quad (3)$$

Figure 5A:
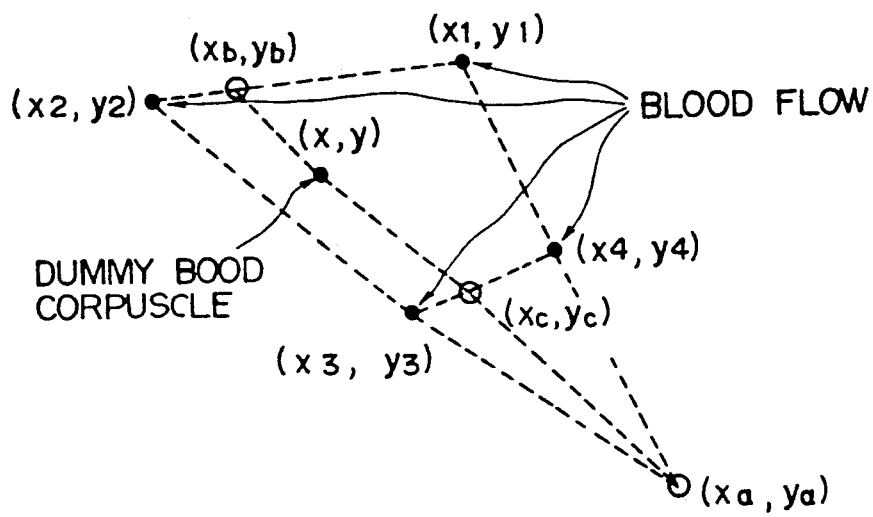
FIGS. 5A and 5B are explanatory diagrams showing another calculation used to obtain a flow velocity vector of dummy blood corpuscle by interpolation.
Figure 5B:
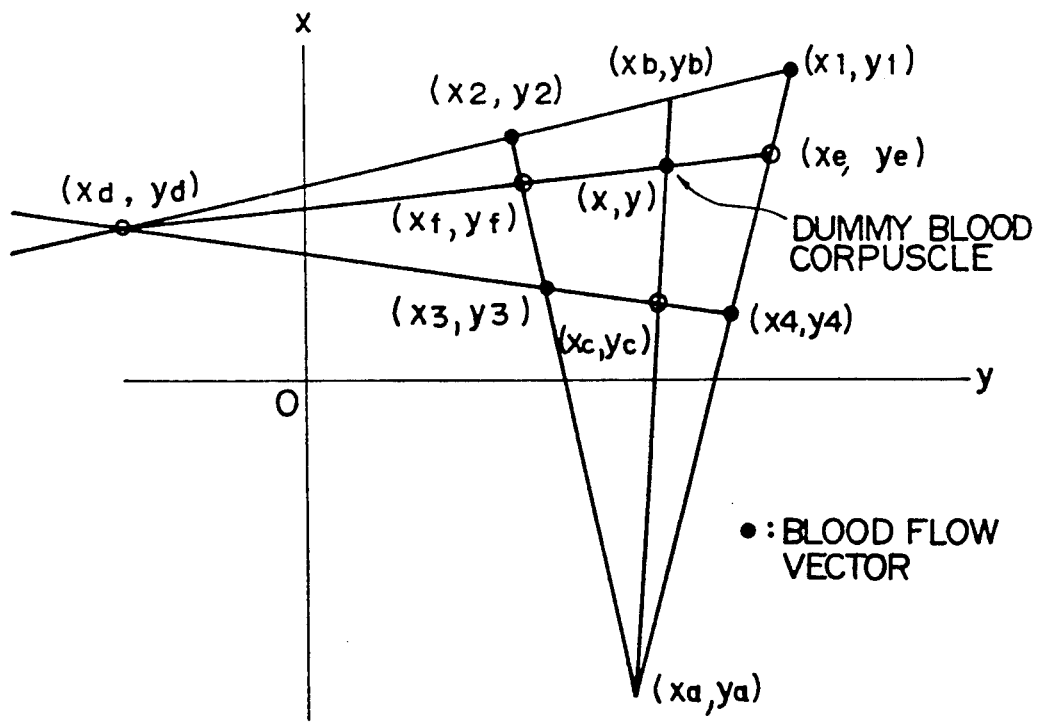

In FIGS. 5A and 5B, another example of the operation for obtaining the flow velocity vector is shown.

In FIG. 5A, first a cross point (Xa, Ya) intersecting a line between positions (X2, Y2) and (X3, Y3) and another line between positions (X1, Y1) and (X4, Y4) is obtained with regard to four positions of the blood flow vectors (X1, Y1), (X2, Y2), (X3, Y3), and (X4, Y4) which are located near the position (X, Y) of the dummy blood corpuscle for which the flow velocity vector is to be obtained.

Then, an intersection (Xb, Yb) of a connecting line between the intersection (Xa, Ya) and the position (X, Y) of the dummy blood corpuscle and another connecting line between the positions (X2, Y2) and (X1, Y1), and another intersection (Xc, Yc) of the connecting line between the intersection (Xa, Ya) and the position (X, Y) and another connecting line between the positions (X3, Y3) and (X4, Y4) are obtained.

Thereafter, the flow velocity vector $V_{(Xb, Yb)}$ of the obtained intersection (Xb, Yb) is obtained from the $V_{(X2, Y2)}$ and $V_{(X1, Y1)}$, and similarly, the flow velocity vector $V_{(Xc, Yc)}$ of the intersection (Xc, Yc) is obtained from and $V_{(X3, Y3)}$ and $V_{(X4, Y4)}$.

Finally, the flow velocity vector $V_{(X, Y)}$ of the dummy blood corpuscle is obtained from the flow velocity vectors $V_{(Xb, Yb)}$ and $V_{(Xc, Yc)}$, and thus the flow velocity vector $V_{(X, Y)}$ of the dummy blood corpuscle in the position (X, Y) obtained. Note the following equations.

Assuming that:

$l_{1b}$: distance between (X1, Y1) and (Xb, Yb),
$l_{2b}$: distance between (X2, Y2) and (Xb, Yb),
$l_{3c}$: distance between (X3, Y3) and (Xc, Yc),
$l_{4c}$: distance between (X4, Y4) and (Xc, Yc),
$l_b$: distance between (X, Y) and (Xb, Yb),
$l_c$: distance between (X, Y) and (Xc, Yc), $$V_{(X,Y)} = \frac{l_c \times V_{(Xb,Yb)} + l_b \times V_{(Xc,Yc)}}{l_b + l_c}.$$

In the above equation, $$V_{(Xb,Yb)} = \frac{l_{2b} \times V_{(X1,Y1)} + l_{1b} \times V_{(X2,Y2)}}{l_{1b} + l_{2b}},$$

$$V_{(Xc,Yc)} = \frac{l_{4c} \times V_{(X3,Y3)} + l_{3c} \times V_{(X4,Y4)}}{l_{3c} + l_{4c}}.$$

In FIG. 5B, using an intersection (Xd, Yd) instead of the intersection (Xa, Ya), the flow velocity vector in the position (X, Y) of the dummy blood corpuscle is similarly obtained by interpolation. The same flow velocity vector is obtained in the above two ways.

Figure 6:
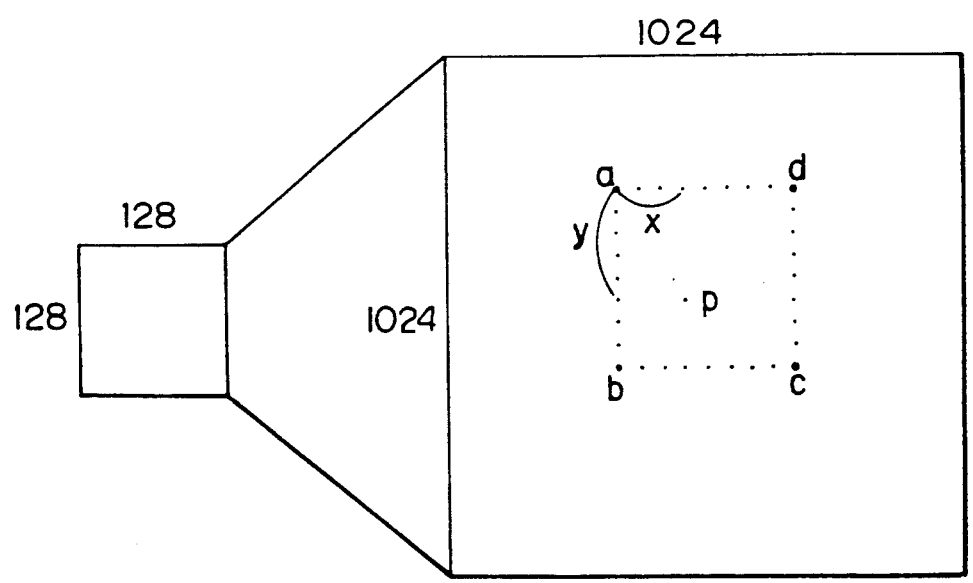
FIG. 6 is an explanatory diagram showing an example of a calculation used to obtain an interpolated data of blood flow vectors.

In FIG. 6, when the amount of data of the blood flow vectors is not sufficient, the interpolation of the data in the state of the blood flow vector is explained.

For example, when the data of 128×128 points is converted to the data of 1024×1024 points by an interpolation, i.e., when the vector component of a position p of the blood flow vector is obtained from blood flow vector components at points a, b, c, and d, the result is expressed by the following equation.

$$p = (xa + (1-x)d).y + (xb + (1-x)c)(1-y)$$

In the equation, x, y > 0 and x, y < 1, i.e., x and y are normalized.

By first executing the above interpolation, the corresponding flowing velocity vector also can be obtained from the interpolated data.

FIG. 7 shows a display using a plurality of images according to this embodiment.

In FIG. 7, phases 1, 2, ..., n correspond to times, for example, sequentially delayed from the time of an R-wave of an electrocardiogram. In each phase, a blood flow vector distribution map 1, and when necessary a blood pressure distribution map 2, are obtained, a plurality of the dummy blood corpuscle images 4-1 to 4-n, respectively, in each phase are formed, and these images are displayed cyclically.

Accordingly, the behavior of the blood flow in phases 1 to n can be sequentially displayed as animated pictures showing the movement of the dummy blood corpuscles.

In this embodiment, as shown in FIG. 1, the ultrasonic pulses reflected from the radiated living body are received and Doppler analyzed, and after a vector forming processing has obtained the blood flow vector distribution map 1, the respective flow velocity vectors of the dummy blood corpuscles are calculated from the blood flow vector distribution map 1 with regard to the arranged dummy blood corpuscles for the whole area (for example, random arranged dummy blood corpuscles). Then, a plurality of images 4-1 to 4-n wherein the dummy blood corpuscles are moved by certain distances in response to the calculated flow velocity vectors are formed and the blood flow is displayed at the display as animated pictures showing the movement of the dummy blood corpuscles. Also, the dummy blood corpuscles are arranged in the area in response to the blood pressure distribution, and similarly, a plurality of images 4-1 to 4-n wherein the dummy blood corpuscles are moved by a certain distance in response to the obtained flow velocity vectors, are formed and displayed.

Further, a plurality of images wherein the dummy blood corpuscles are sequentially moved in accordance with the blood flow obtained at a predetermined phase, e.g., R-wave phase of the electrocardiogram, and when necessary the obtained blood pressure, are formed. Then, a plurality of images are formed wherein the dummy blood corpuscles are sequentially moved at different phases, and the images are continuously displayed. By using this invention, a position of a myocardial infraction can be examined, and further, the valve paresis is easily examined.

In addition, the pressure is obtained from the velocity distribution and time variations thereof, by the following equations (Navier-Stokes).

$$\frac{\partial u}{\partial t} + u \frac{\partial u}{\partial x} + v \frac{\partial u}{\partial y} = -\frac{1}{\rho} \frac{\partial p}{\partial x} + \nu \nabla^2 u$$

$$\frac{\partial v}{\partial t} + u \frac{\partial v}{\partial x} + v \frac{\partial v}{\partial y} = -\frac{1}{\rho} \frac{\partial p}{\partial y} + \nu \nabla^2 v$$

u, v: velocity,
p: pressure,
$\nu$: dynamic viscosity factor,
$\nabla^2$: Laplacian,
$\rho$: density By solving the above equation, the relative value of the pressure can be obtained.

We claim:

1. A method of making visible a flow of blood in a living body, comprising the steps of:
   obtaining a plurality of blood flow vector distribution maps by using a plurality of reflected waves received from the living body to which a plurality of ultrasonic pulses are radiated, and by using a Doppler analysis of the plurality of reflected waves;
   arranging a plurality of dummy blood corpuscles in a plurality of domains in which the plurality of blood flow vector distribution maps are expressed;
   calculating a plurality of flow velocity vectors of the plurality of dummy blood corpuscles for each of the plurality of dummy blood corpuscles from each of the plurality of blood flow vector distribution maps;
   forming a plurality of images in which the plurality of dummy blood corpuscles are sequentially moved in response to the plurality of flow velocity vectors; and
   sequentially displaying the plurality of images on a display.

2. A method as set forth in claim 1, wherein said calculation of at least one of the plurality of flow velocity vectors of one of the plurality of dummy blood corpuscles is carried out by an interpolation using adjacent blood flows in one of the plurality of blood flow vector distribution maps.

3. A method as set forth in claim 2,
   wherein the plurality of images in which the plurality of dummy blood corpuscles are moved sequentially in predetermined phases are formed,
   wherein the sequential movement of the plurality of dummy blood corpuscles in different phases is repeated, and
   wherein the plurality of images is continuously displayed.

4. A method as set forth in claim 1, wherein one of said plurality of blood flow vector distribution maps is obtained by an interpolation of data reflected from the living body.

5. A method as set forth in claim 4,
   wherein the plurality of images in which the plurality of dummy blood corpuscles are moved sequentially in predetermined phases are formed,
   wherein the sequential movement of the plurality of dummy blood corpuscles in different phases is repeated, and
   wherein the plurality of images is continuously displayed.

6. A method as set forth in claim 1,
   wherein a blood pressure is obtained from one of said plurality of blood flow vector distribution maps, and
   wherein a density of an arrangement of the plurality of dummy blood corpuscles corresponds to the blood pressure.

7. A method as set forth in claim 6,
   wherein the plurality of images in which the plurality of dummy blood corpuscles are moved sequentially in predetermined phases are formed,
   wherein the sequential movement of the plurality of dummy blood corpuscles in different phases is repeated, and
   wherein the plurality of images is continuously displayed.

8. A method as set forth in claim 1,
   wherein a plurality of images in which the plurality of dummy blood corpuscles are moved sequentially in predetermined phases are formed,
   wherein the sequential movement of the plurality of dummy blood corpuscles in different phases is repeated, and
   wherein the plurality of images is continuously displayed.

9. A method as set forth in claim 1, wherein the display of the plurality of images of the plurality of dummy blood corpuscles is selected from at least one of a blood flow vector display and a blood pressure display obtained from one of the plurality of blood flow vector distribution maps.

10. A system for making visible a flow of blood in a living body using a plurality of ultrasonic pulses, comprising:
- ultrasonic transmission/reception means for radiating the plurality of ultrasonic pulses to the living body, for receiving a plurality of reflected waves from the living body, for Doppler analyzing the plurality of reflected waves, and for carrying out a process to form a plurality of blood flow vectors to thereby obtain a blood flow vector distribution map;
- two-dimensional vector memory means for storing the blood flow vector distribution map obtained from said ultrasonic transmission/reception means, and for providing a first output and a second output;
- calculation means for receiving the first output, for calculating data based on the first output, and for forming a two-dimensional dynamic pressure distribution map;
- two-dimensional pressure distribution memory means for storing the two-dimensional dynamic pressure distribution map supplied by said calculation means, and for providing a third output;
- dummy blood corpuscle generation means for receiving the third output, for forming a plurality of dummy blood corpuscles in response to the third output, and for providing a fourth output;
- two-dimensional dummy blood corpuscle distribution memory means for storing a two-dimensional distribution of the fourth output, and for providing a fifth output;
- dummy blood corpuscle movement processor means for receiving the fifth output and the second output, and for forming a plurality of respective flow velocity vectors for each of the plurality of dummy blood corpuscles from the plurality of blood flow vectors of the blood flow vector distribution map; and
- dummy blood corpuscle movement memory means for storing respective images obtained by sequentially moving the dummy blood corpuscles by an amount based on the flow velocity vector, and for providing a sixth output;
- whereby the sixth output is sequentially read so that a movement of the flow of blood is detected.

11. A method for generating a plurality of data representing a plurality of blood corpuscles by using a two-dimensional blood pressure distribution including a plurality of coordinates which each have one of a plurality of blood pressure values, comprising the steps of:
a) arranging a plurality of data representing a presence of each of the plurality of blood corpuscles at each of the plurality of coordinates;
b) assigning one of a plurality of uniform random numbers to each of the plurality of data representing the presence of each of the plurality of blood corpuscles;
c) determining whether the one of the plurality of uniform random numbers assigned to each of the plurality of data representing the presence of each of the plurality of blood corpuscles is less than the one of the plurality of blood pressure values assigned to each of the plurality of coordinates on which each of the plurality of data representing the presence of each of the plurality of blood corpuscles are arranged to provide a result; and
d) eliminating selected ones of the plurality of data representing the presence of each of the plurality of blood corpuscles based on the result of said step (c).

12. A method for displaying a movement of matter in a living body using pulses, comprising the steps of:
a) transmitting pulses to the living body;
b) receiving a reflected pulses from the living body;
c) compiling a vector distribution based on the received reflected pulses;
d) introducing a dummy object to the vector distribution;
e) calculating a distance of movement of the dummy object in response to the vector distribution for a predetermined time period; and
f) displaying a location of the dummy object after the predetermined period.

13. A method as set forth in claim 12, wherein steps (a)-(f) are repeatedly executed.

* * * * *